US010007856B2

(12) United States Patent
Robles-Kelly et al.

(10) Patent No.: US 10,007,856 B2
(45) Date of Patent: Jun. 26, 2018

(54) PROCESSING HYPERSPECTRAL OR MULTISPECTRAL IMAGE DATA

(71) Applicant: National ICT Australia Limited, Eveleigh NSW (AU)

(72) Inventors: Antonio Robles-Kelly, Eveleigh (AU); Johannes Jordan, Eveleigh (AU)

(73) Assignee: NATIONAL ICT AUSTRALIA LIMITED, Eveleigh, New South Wales (AU)

( * ) Notice: Subject to any disclaimer, the term of this patent is extended or adjusted under 35 U.S.C. 154(b) by 21 days.

(21) Appl. No.: 15/118,643

(22) PCT Filed: Feb. 13, 2015

(86) PCT No.: PCT/AU2015/050052
§ 371 (c)(1),
(2) Date: Aug. 12, 2016

(87) PCT Pub. No.: WO2015/120519
PCT Pub. Date: Aug. 20, 2015

(65) Prior Publication Data
US 2017/0053178 A1 Feb. 23, 2017

(30) Foreign Application Priority Data

Feb. 14, 2014 (AU) ................. 2014900461

(51) Int. Cl.
*G06K 9/00* (2006.01)
*G06K 9/20* (2006.01)
(Continued)

(52) U.S. Cl.
CPC ............. *G06K 9/2018* (2013.01); *G06K 9/46* (2013.01); *G06K 9/4652* (2013.01);
(Continued)

(58) Field of Classification Search
CPC .. G06K 9/6218; G06K 9/6215; G06K 9/6267; G06K 9/00288; G06K 9/6223; G06K 9/6276
See application file for complete search history.

(56) References Cited

U.S. PATENT DOCUMENTS

| 8,811,754 B2* | 8/2014 | Conger | ................ G06K 9/2018 382/225 |
| 2004/0151384 A1* | 8/2004 | Yang | .................. G06K 9/00275 382/225 |

(Continued)

FOREIGN PATENT DOCUMENTS

WO   WO 2011/130793   10/2011

OTHER PUBLICATIONS

Polikar, R. "Ensemble Based Systems in Decision Making"; *IEEE Circuits and Systems Magazines*; pp. 21-44; 2006, (Sep. 2006).

(Continued)

*Primary Examiner* — Eueng-Nan Yeh

(57) ABSTRACT

The disclosure concerns processing hyperspectral or multispectral images. Image data comprises a sampled image spectrum represented by first values for each pixel location representative of an intensity associated with a wavelength index. A processor determines for each pixel location second values based on a measure of similarity between pixel locations with respect to the first values such that two pixel locations that 5 are similar with respect to the first values are also similar with respect to the second values. The processor then stores for each pixel location the determined one or more second values associated with that pixel location on a data store. This way, the image data is made suitable for applications, such as clustering or displaying, while pixels that are similar in the input image are also similar in the (Continued)

output data. This means that a 10 structure between the pixels in the input image is preserved.

13 Claims, 10 Drawing Sheets

(51) Int. Cl.
    *G06K 9/46*     (2006.01)
    *H04N 1/60*     (2006.01)
    *H04N 1/64*     (2006.01)
    *G06K 9/62*     (2006.01)
    *G06T 7/90*     (2017.01)
    *G06T 7/40*     (2017.01)
    *G01J 3/28*     (2006.01)

(52) U.S. Cl.
    CPC ............ *G06K 9/6224* (2013.01); *G06T 7/408* (2013.01); *G06T 7/90* (2017.01); *H04N 1/6086* (2013.01); *H04N 1/644* (2013.01); *G01J 3/2823* (2013.01); *G06T 2207/10024* (2013.01)

(56) References Cited

U.S. PATENT DOCUMENTS

| | | | |
|---|---|---|---|
| 2006/0084125 A1* | 4/2006 | Laor | G01N 33/57407 435/7.23 |
| 2011/0222785 A1* | 9/2011 | Hirohata | G06K 9/00288 382/224 |
| 2012/0200682 A1 | 8/2012 | Mestha et al. | |
| 2013/0039580 A1 | 2/2013 | Robles-Kelly et al. | |
| 2013/0201342 A1 | 8/2013 | Skaff et al. | |
| 2013/0272617 A1 | 10/2013 | Conger | |

OTHER PUBLICATIONS

International Search Report; PCT/AU2015/050052; 13 pages; dated Mar. 31, 2015.

\* cited by examiner

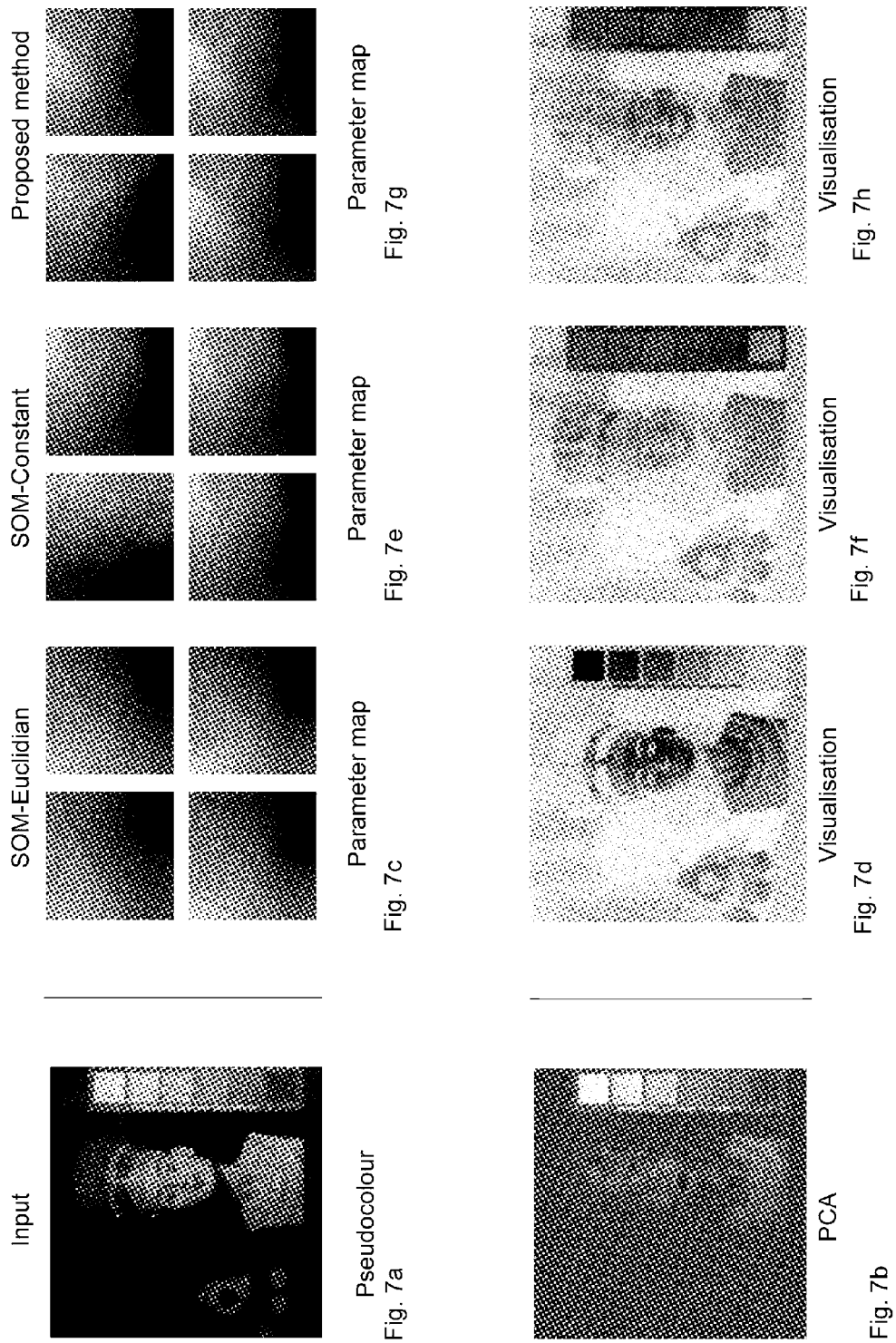
Fig. 7a Input
Fig. 7b PCA
Fig. 7c SOM-Euclidian Parameter map
Fig. 7d Visualisation
Fig. 7e SOM-Constant Parameter map
Fig. 7f Visualisation
Fig. 7g Proposed method Parameter map
Fig. 7h Visualisation
Pseudocolour

PROCESSING HYPERSPECTRAL OR MULTISPECTRAL IMAGE DATA

CROSS-REFERENCE TO RELATED APPLICATIONS

The present application claims priority from Australian Provisional Patent Application No 2014900461 filed on 14 Feb. 2014, the content of which is incorporated herein by reference.

TECHNICAL FIELD

The disclosure concerns processing of electronic images, such as hyperspectral or multispectral images. In particular the invention concerns, but is not limited to, methods, software and computer systems for processing hyperspectral or multispectral images.

BACKGROUND ART

Imaging spectroscopy relies on associating each pixel in the image with a spectrum representing the intensity at each wavelength. As a result, imaging spectroscopy provides an information-rich representation of the scene which combines spatial and compositional information which can be used for a wide variety of applications spanning from remote sensing to food security and health.

For spectral image classification, each pixel spectra can be viewed as an input vector in a high dimensional space. This treatment opens up the possibility of representing a scene in terms of a number of spectral prototypes which correspond to naturally occurring materials such as wood, paint, etc. These materials can be extracted from the scene and are, in general, unknown a priori. Moreover, these material prototypes should be consistent across pixels sharing similar spectra.

FIG. 1 illustrates a transformation 100 of first and second pixel radiance spectra 110 and 120 respectively, into a spectral space 130. The first pixel radiance spectrum 110 is sampled at two wavelengths $\lambda_1$ and $\lambda_2$. This results in radiance values 111 and 112. The radiance values 111 and 112 of the first pixel are represented by a first sample 131 in the two-dimensional spectral space 130.

Similarly, the second pixel radiance spectrum 120 is sampled at the same two wavelengths $\lambda_1$ and $\lambda_2$ resulting in radiance values 121 and 122, which are represented by a second sample 132 in the spectral space 130. In this way, the radiance spectra of many pixels can be represented in the same spectral space 130.

by a second sample 132 in the spectral space 130. In this way, the radiance spectra of many pixels can be represented in the same spectral space 130.

It is noted that in most applications the radiance spectra are sampled at far more points, such as one hundred. In fact, the sample wavelengths may be the same as the wavelengths of the hyperspectral image data. As a result, the sample space 130 is high-dimensional—one dimension for each wavelength.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DISCLOSURE OF INVENTION

There is provided a computer implemented method for processing hyperspectral or multispectral image data. The image data comprises for each pixel location a sampled image spectrum that comprises multiple first values for each pixel location such that each of the multiple first values is representative of an intensity associated with a wavelength index.

The method comprises:
  determining for each pixel location one or more second values based on a measure of similarity between pixel locations with respect to the multiple first values such that two pixel locations that are similar with respect to the multiple first values are also similar with respect to the one or more second values; and
  storing for each pixel location the determined one or more second values associated with that pixel location on a data store.

In many cases the hyperspectral or multispectral image data is not suitable for a particular purposes. For example, clustering of hyperspectral image data is difficult due to the curse of dimensionality or using an RGB computer screen is difficult for RGBD image data. With the method above the image data can be processed such that it is suitable for the particular purpose. At the same time, this processing is based on a measure of similarity of the pixels of the input image. As a result, pixels that are similar in the input image are also similar in the output data. This also means that a structure between the pixels in the input image is preserved. The advantage is that the output data is more useful and more accurate than other mapping methods.

The measure of similarity between pixel locations with respect to the multiple first values may be based on a coding vector for each pixel location from the multiple first values to the one or more second values.

The measure of similarity between pixel locations with respect to the multiple first values may be based on a distance measure between the multiple first values and the coding vector.

Determining the one or more second values may comprise determining the coding vector. Determining the coding vector may comprise performing a maximum likelihood estimation.

Performing the maximum likelihood estimation may comprise performing an Expectation Maximisation method.

Performing the Expectation Maximisation method may comprise performing an Expectation step by determining an updated mapping vector and an updated mixture weight in relation to the one or more second values and performing a Maximisation step by determining a posterior of each clique of pixel locations.

The method may further comprise determining mixture weights in relation to the one or more second values by applying a self organising map.

The number of the one or more second values may be less than the number of the multiple first values.

The method may further comprise determining multiple clusters of the pixel locations based on the one or more second values and associating a material spectrum with each cluster.

The method may further comprise outputting a visual image of the image data by using the one or more second values as intensity values for one or more respective output channels.

The one or more second values may comprise red, green and blue values.

The number of the multiple first values may be more than 7.

Software, when executed by a computer, causes the computer to perform the method of any one of the preceding claims.

A computer system for processing hyperspectral or multispectral image data comprises:
a data port to receive the image data comprising for each pixel location a sampled image spectrum that comprises multiple first values for each pixel location such that each of the multiple first values is representative of an intensity associated with a wavelength index;
a processor to determine for each pixel location one or more second values based on a measure of similarity between pixel locations with respect to the multiple first values such that two pixel locations that are similar with respect to the multiple first values are also similar with respect to the one or more second values; and
a data store to store for each pixel location the determined one or more second values associated with that pixel location.

Optional features described of any aspect of method, computer readable medium or computer system, where appropriate, similarly apply to the other aspects also described here.

An example will be described with reference to

Figure 2:
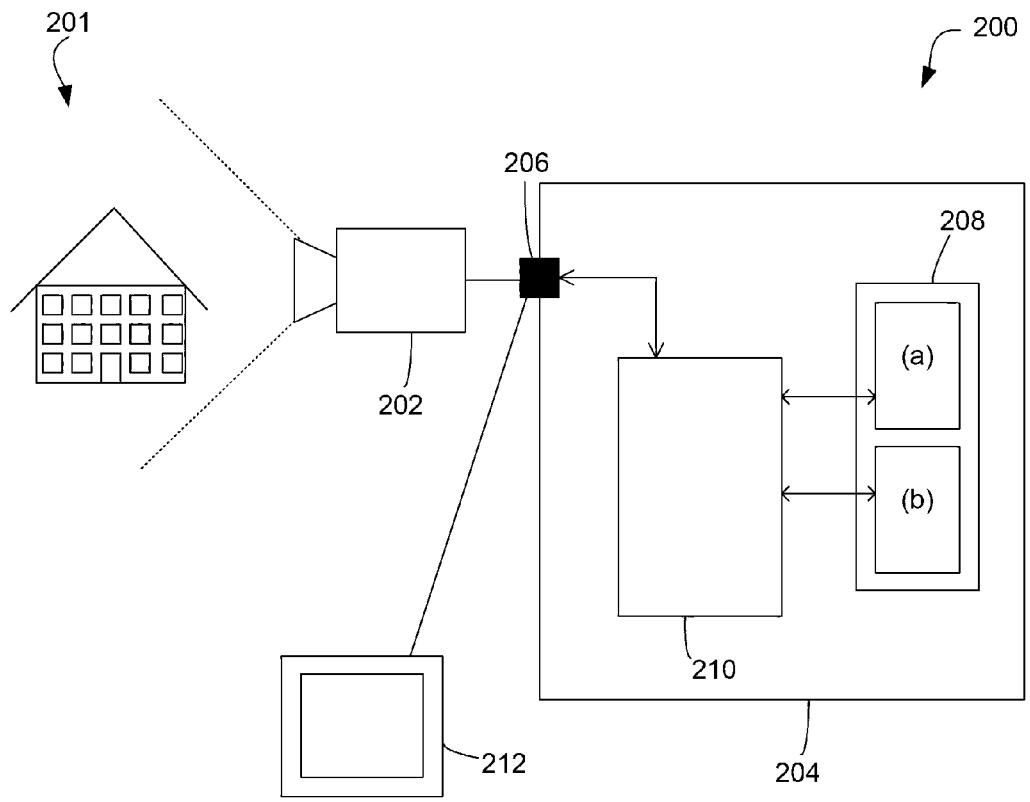

FIG. 2 illustrates a computer system for processing hyperspectral or multispectral image data.

Figure 3:
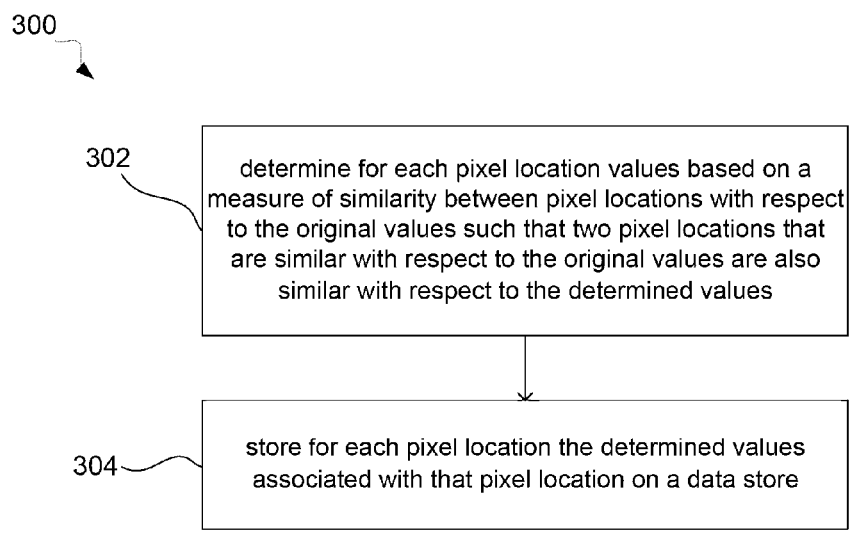

FIG. 3 illustrates a computer implemented method for processing hyperspectral or multispectral image data.

Figure 4:
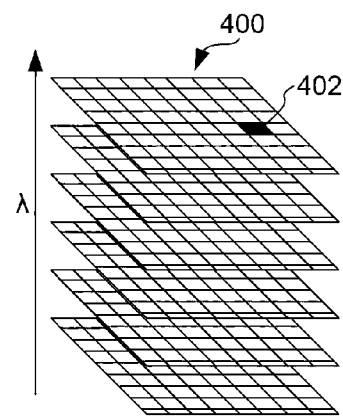

FIG. 4 illustrates a data structure for multispectral image data.

Figure 5:
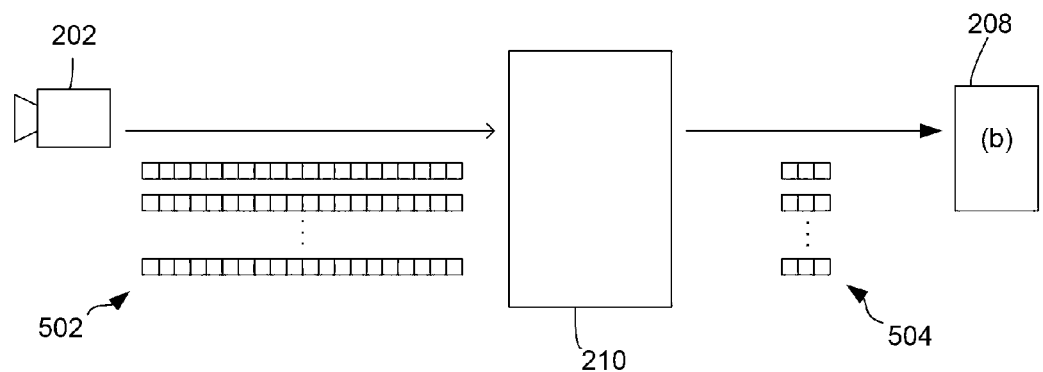

FIG. 5 illustrates an example data flow.

Figure 6A:
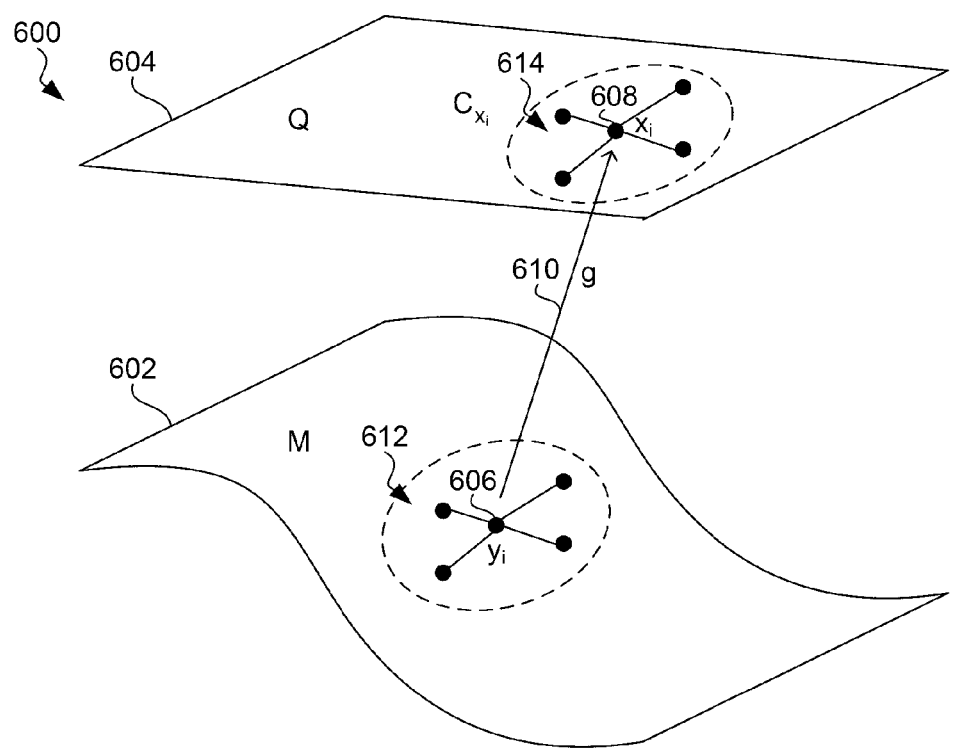

FIG. 6 illustrates a graphical representation of the calculations performed by the processor in FIG. 2.

FIGS. 7a to 7h illustrate 2-dimensional responses.

Figure 8C:
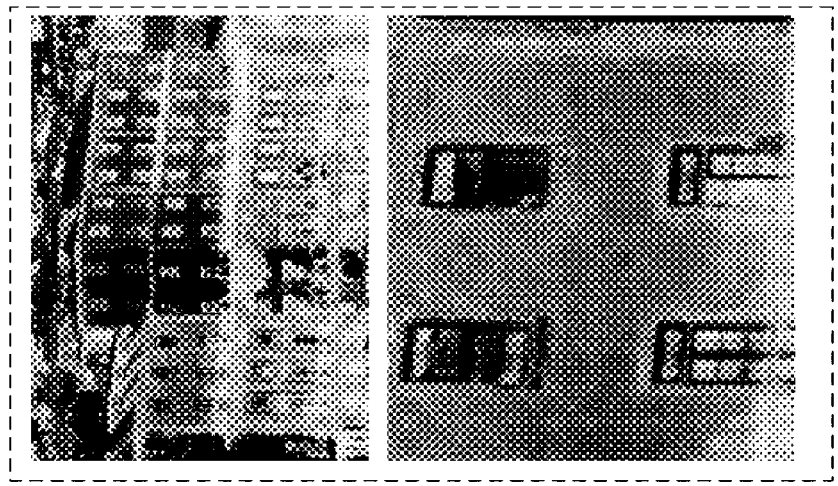
Figure 8B:
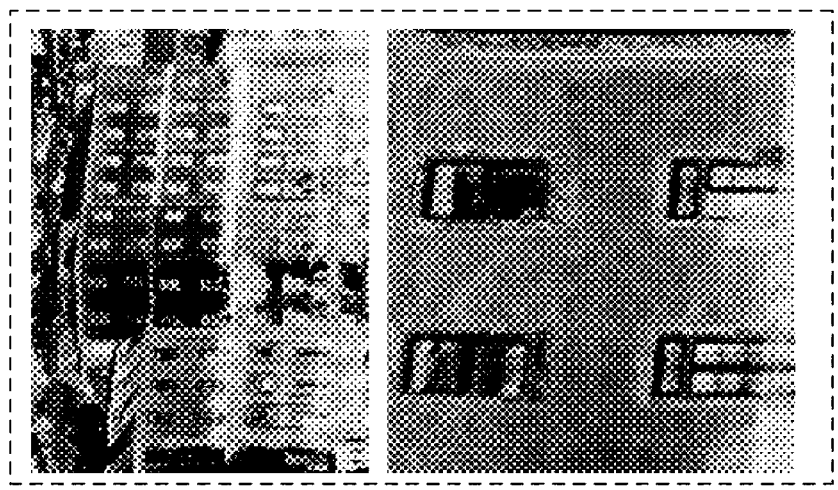
Figure 8A:
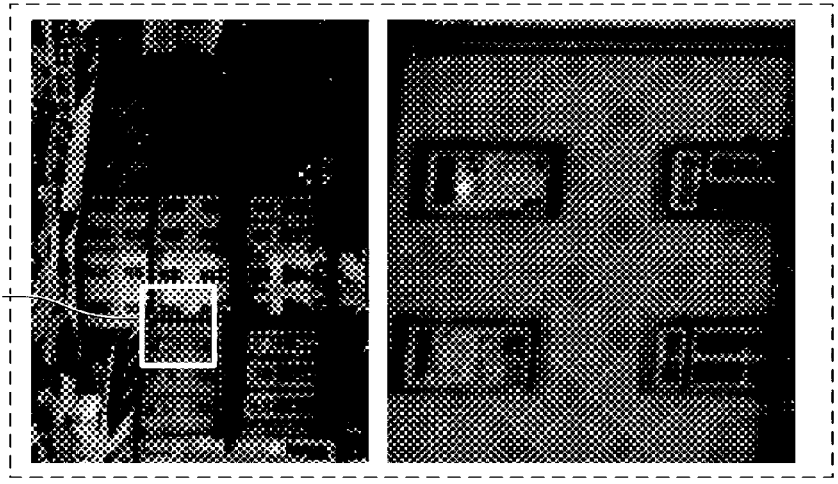

FIGS. 8a, 8b and 8c illustrate the coding vectors for a natural scene.

Figure 9A:
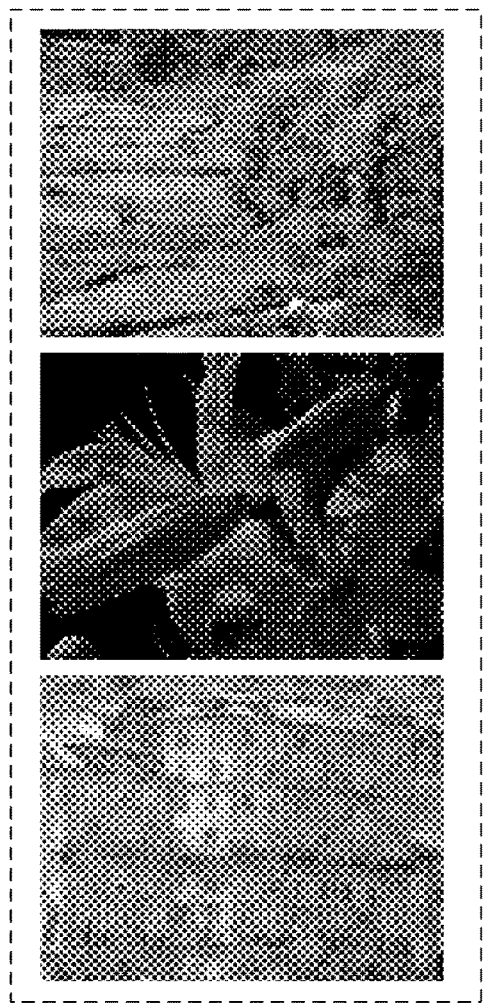

FIG. 9a illustrates three example inputs.

Figure 9B:

FIG. 9b illustrates material segmentation results for the example inputs of FIG. 9a.

Figure 10A:
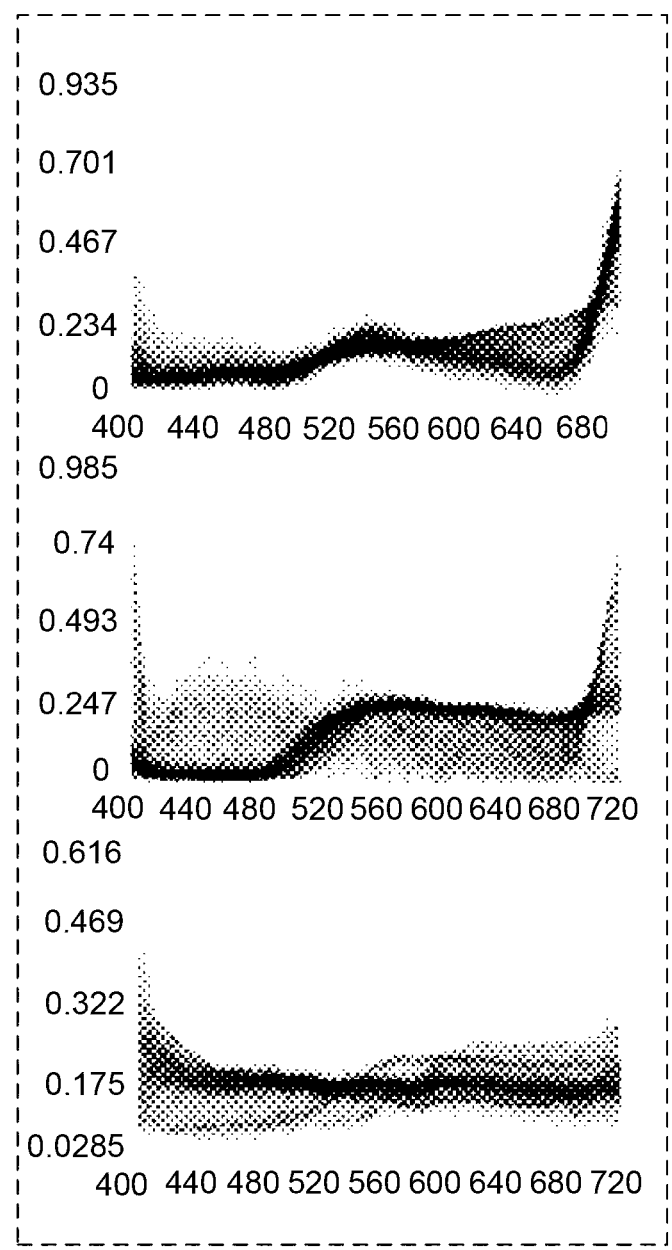
Figure 10B:
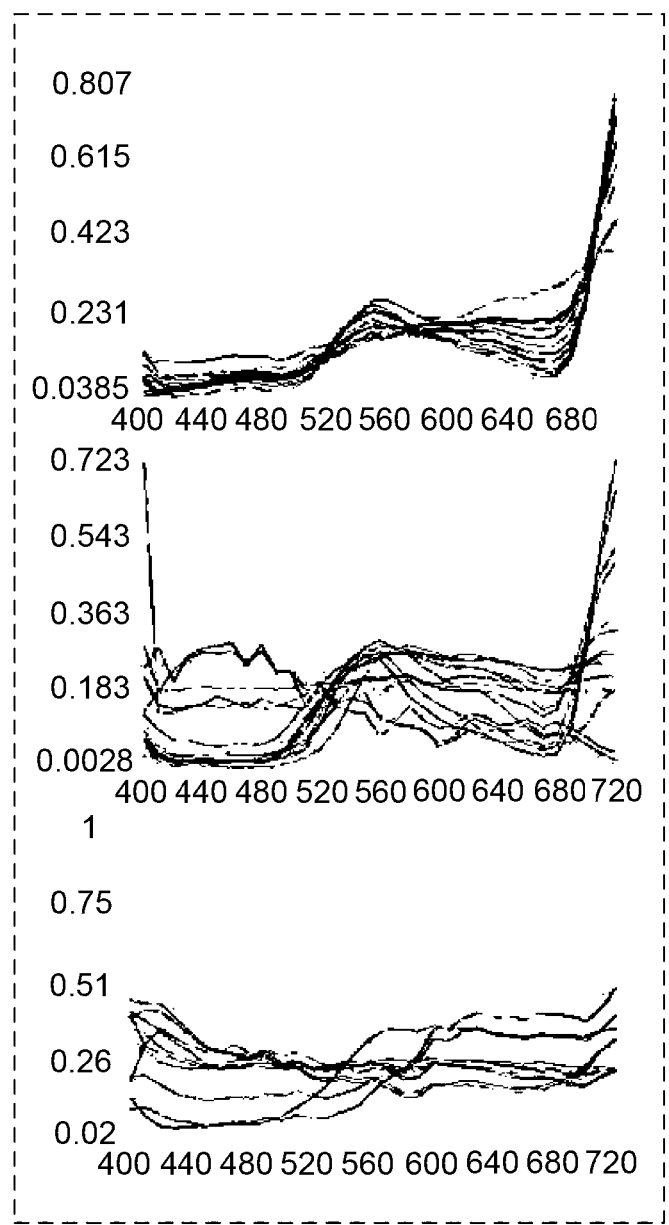

FIGS. 10a and 10b depicts the material prototypes found in the images as shown in FIG. 9a.

Figure 11A:
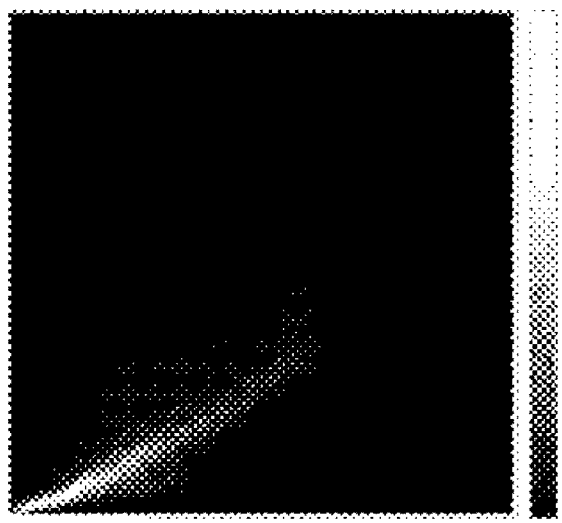
Figure 11B:
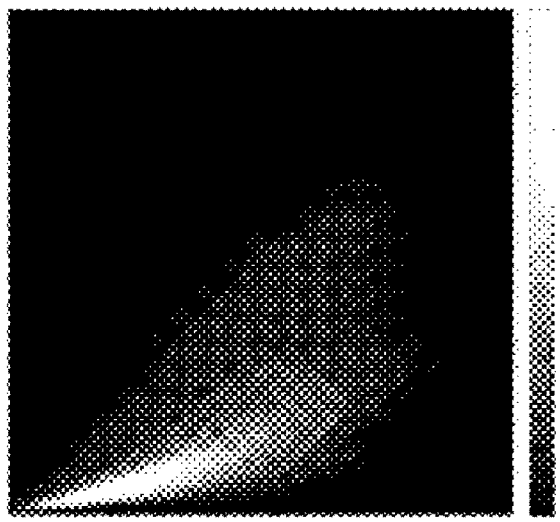
Figure 11C:
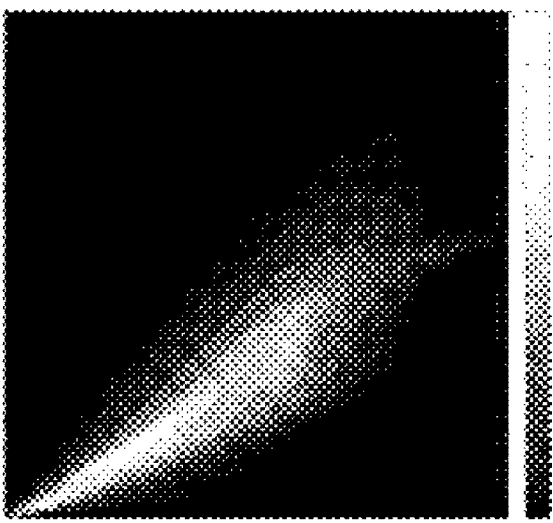

FIGS. 11a, 11b and 11c illustrate scatter plot histograms for the pairwise distances.

BEST MODE FOR CARRYING OUT THE INVENTION

FIG. 2 illustrates a computer system 200 for processing hyperspectral or multispectral image data of a scene 201. Computer system 200 comprises a sensor 202 and a computer 204. In this example the sensor 202 is a hyperspectral or multispectral sensor that is able to capture an image of a scene 201.

In one example, the computer system 200 is integrated into a handheld device such as a consumer camera and the scene 201 may be any scene on the earth, such as a tourist attraction or a person. The sensor 202 may have a number of bands that balances computational costs with accuracy. The sensor 202 may have as low as four bands, such as red, green, blue and depth, or as high as hundreds. In one example, sensor 202 is a Fluxdata camera FD-1665-MS7.

The computer 204 receives images from the sensor 202 via a data port 206 and the images are stored in local memory 208(b) by the processor 210. The processor 210 uses software stored in memory 208(a) to perform the method shown in FIG. 5. The program memory 208(b) is a non-transitory computer readable medium, such as a hard drive, a solid state disk or CD-ROM.

The processor 210 performs the method 300 in FIG. 3 of processing the image data received from sensor 202. Processor 210 determines for each pixel location values ($x_i$) based on a measure of similarity between pixel locations with respect to the original values such that two pixel locations that are similar with respect to the original values are also similar with respect to the determined values. Processor 210 then stores for each pixel location the determined one or more second values associated with that pixel location on a data store.

Processor 210 may use the processed and stored data to perform clustering for material recognition. Processor 210 may also generate a visualisation based on the determined values. In particular, processor 210 may determine three values for each pixel location and may use these three values as red, green and blue values of a display device 212.

In one example, processor 210 performs on each cluster a method for estimating an illumination spectrum of an image as described in WO 2011/026167 "Illumination Spectrum Recovery", which is incorporated herein by reference. Further, processor 210 may perform a method for decomposing hyperspectral or multispectral image data as described in U.S. Pat. No. 8,670,620 "Decomposing hyperspectral or multispectral image data", which is incorporated herein by reference. For storing the input spectra, illumination spectra or other spectra the computer may employ the method described in WO 2009/152583 "Compact Representation of a Reflectance Spectrum" which is incorporated herein by reference.

The software provides a user interface that can be presented to the user on a monitor 212. The user interface is able to accept input from the user (i.e. touch screen). The user input is provided to the input/out port 206 by the monitor 212. The image is stored in memory 208(b) by the processor 210. In this example the memory 208(b) is local to the computer 204, but alternatively could be remote to the computer 204.

The processor 210 may receive data, such as image data, from data memory 208(b) as well as from the communications port 206. In one example, the processor 210 receives image data from the sensor 202 via communications port 206, such as by using a Wi-Fi network according to IEEE 802.11. The Wi-Fi network may be a decentralised ad-hoc network, such that no dedicated management infrastructure, such as a router, is required or a centralised network with a router or access point managing the network.

In one example, the processor 210 receives and processes the image data in real time. This means that the processor 210 determines the values every time the image data is received from sensor 202 and completes this calculation before the sensor 202 sends the next image data update. In particular, processor 210 may calculate the values for image frames of a video stream.

Although communications port 206 is shown as single entity, it is to be understood that any kind of data port may be used to receive data, such as a network connection, a memory interface, a pin of the chip package of processor 210, or logical ports, such as IP sockets or parameters of functions stored on program memory 208(a) and executed by processor 210. These parameters may be stored on data memory 208(b) and may be handled by-value or by-reference, that is, as a pointer, in the source code.

The processor 210 may receive data through all these interfaces, which includes memory access of volatile memory, such as cache or RAM, or non-volatile memory, such as an optical disk drive, hard disk drive, storage server or cloud storage. The computer system 204 may further be implemented within a cloud computing environment, such as a managed group of interconnected servers hosting a dynamic number of virtual machines.

It is to be understood that any receiving step may be preceded by the processor 210 determining or computing the data that is later received. For example, the processor 210 determines the image data, such as by filtering the raw data from sensor 202, and stores the image data in data memory 208(b), such as RAM or a processor register.

The processor 210 then requests the data from the data memory 208(b), such as by providing a read signal together with a memory address. The data memory 208(b) provides the data as a voltage signal on a physical bit line and the processor 210 receives the image data via a memory interface.

FIG. 3 illustrates a computer implemented method 300 for processing hyperspectral or multispectral image data. FIG. 3 is to be understood as a blueprint for image processing software program, such as part of camera firmware or a processing pipeline. Method 300 may be implemented step-by-step, such that each step in FIG. 3 is represented by a then compiled and stored as computer executable instructions on program memory 208(b).

It is noted that for most humans performing the method 300 manually, that is, without the help of a computer, would be practically impossible. Therefore, the use of a computer is part of the substance of the invention and allows performing the necessary calculations that would otherwise not be possible due to the large amount of data and the large number of calculations that are involved.

Before commencing the execution of method 300, processor 210 receives the hyperspectral or multispectral image data from sensor 202.

FIG. 4 illustrates a data structure 400 for the multispectral image data. The data structure 400 comprises layers, one for each wavelength. Each layer comprises input values that are representative of the intensity associated with a wavelength index. One example pixel 402 is highlighted. The input values of pixel 402 associated with different wavelengths, that is the radiance input values from lower layers at the same location as pixel 402, represent a radiance spectrum also referred to as the image spectrum or input spectrum. This input spectrum may be a mixture of multiple illumination spectra and the reflectance spectra of different materials present in the part of the scene that is covered by pixel 402.

In the following description, the term 'pixel location' refers to an index of image data that can be mapped to a particular location of the image. A pixel location may refer to the data from an individual imaging element of sensor 202, that is, a camera pixel, or to individually addressable image elements that may be computed based on multiple camera pixels. For example, the image resolution may be reduced by combining pixels and the method 300 is performed on the low-resolution image having multiple points instead of pixels.

Referring back to method 300 in FIG. 3, processor 210 determines 302 for each pixel location one or more values that will later be labelled $x_i$. This calculation is based on a measure of similarity between pixel locations with respect to the input values. The calculation based on the measure of similarity ensures that two pixel locations that are similar with respect to the input values are also similar with respect to the determined values.

In one example, the input image data has hundreds of bands. As a result, clustering the input image data is difficult because most clustering methods rely on some sort of distance measure and most distance measures become meaningless with a high dimensional dataset. This is also referred to as "curse of dimensionality". Method 300 can be applied as a dimension reduction technique to facilitate clustering on the determined values for each pixel. Each cluster may then be associated with a material spectrum.

Further, with hundreds of bands, it is difficult to visualise the image data as most screens only provide three channels, such as red, green and blue (RGB). Method 300 can be applied to determine three values for each pixel location which may be directly used as RGB.

FIG. 5 illustrates an example data flow 500 through computer 204. Sensor 202 generates image data 502 comprising 20 input values (columns) for each pixel location (rows). Processor 210 determines output data 504 comprising three output values (columns) for each pixel location (rows). Processor 210 stores 304 for each pixel location the determined values 504 on data memory 208(b). In this example, the data stored on data memory 208(a) is an RGB image, such as a TIFF image.

Figure 1:
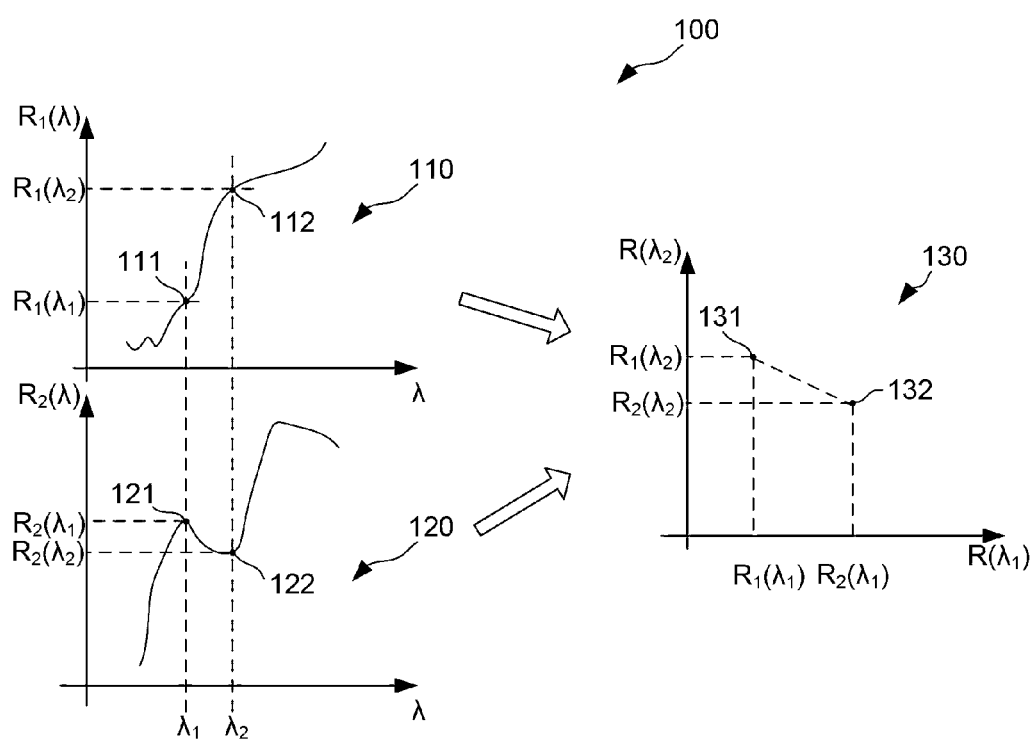
FIG. 1 illustrates a transformation of two pixel radiance spectra into a spectral space.

FIG. 6 illustrates a graphical representation of the calculations performed by processor 210. FIG. 6 comprises an input space 602 and an output space 604. The example of FIG. 6 shows five pixels represented by dots, such as example pixel 606 in the input space 602, which corresponds to pixel 608 in the output space 604. Input space 602 and output space 604 are each similar to space 130 explained with reference to FIG. 1. In other words, each dot represents multiple pixel values.

Processor 210 determines a coding vector that can be multiplied with pixel values 606 of the input space and the result is the pixel values 608 of the output space 604 as represented by arrow 610. The coding vector may also be referred to as parameter vector. As explained further below, processor 210 determines the coding vector using a maximum likelihood estimation including an expectation maximisation method. This process is based on a distance between the coding vector and the and the input values less from the curse of dimensionality and therefore, the proposed method works more accurately and is computationally less complex than clustering the input data directly.

Method 300 can be considered as a method for learning the materials in a scene in an unsupervised manner making use of imaging spectroscopy data. Here, processor 210 uses the input image spectra as a data point on a manifold 602 which corresponds to a node in a graph whose vertices correspond to a set of parameters that should be inferred using the Expectation Maximisation (EM) algorithm. In this manner, processor 210 can perform statistical unsupervised learning where the aim of computation becomes the recovery of the set of parameters that allow for the image spectra to be projected onto a set of graph vertices defined a priori.

Moreover, as a result of this treatment, the scene material prototypes can be recovered making use of a clustering algorithm applied to the parameter-set. This setting also allows, in a straightforward manner, for the visualisation of the spectra.

The use of the coding vectors, which may also referred to as parameter vectors, has two main advantages. Firstly, it facilitates for the visualisation of the image spectra. Secondly, the material prototypes can be recovered using clustering methods, such as mean shift. Moreover, by using a graph theoretic setting, the inference process is a structured one which explicitly includes topological information, preserving similarity relations between input spectra.

The problem in hand can be cast into a graph-theoretic setting, where the samples in the input, i.e. the image spectra, and output spaces are the node-sets of two graphs and the corresponding sets of edge weights are the affinities or "distances" between their spectra. In other words, pixel values with a similar spectra have edges with high weights between them while pixel values that are different have edges weighted with almost zero. In fact, since most of the pixels have different spectra to most other pixels, the edges can be stored as a sparse data structure, which implicitly assigns an edge weight of zero to edges between different spectra. Each of these graphs are hence comprised by an vertex-set, edge-set and edge-weight function set.

Moreover, let these two graphs be $G_M$ 612 and $G_Q$ 614 in FIG. 6, which shows these two graphs, each of which is realised in disjoint manifolds, i.e. $M \in \Re^m$ 602 and $Q \in \Re^q$ 604. This formalism is important since, processor 210 can use the metrics on these manifolds to calculate the affinities between vertices in each graph. In FIG. 6, the vertex-sets for both graphs are linked in a pairwise manner such that $$x_j = \sum_{y_k \in Y} \mathbb{I}(x_j \sim y_j) \Gamma(y_k) \quad (1)$$

where Y is the vertex set of $G_M$, $\delta(\bullet)$ is a mapping function such that $\Gamma: \Re^m \mapsto \Re$ and $\mathbb{I}(x_j \sim y_j)$ is an indicator function which is unity if $x_j$ is adjacent to $y_j$ and zero otherwise.

We now view the graph $G_Q$ as a Gibbs Field. By viewing the vertices of the graph as random variables, the joint probability in a Gibbs Field can be written as the product of clique potentials, i.e. any fully connected subset of the graph. Consider the clique $C_{x_i}$ centred at the vertex $x_i$. Processor 210 can now compute the conditional probability of the vertex under consideration as a weighted product of the pairwise potentials as follows $$P(x_i \mid C_{x_i}) = \frac{1}{Z_Q} \prod_{x_j \in C_{x_i}} f_Q(x_j, x_i) \quad (2)$$

where, $Z_Q$ is the partition function and $f_Q(x_j, x_i)$ is the potential function between the vertices $x_j$ and $x_j$.

Note that the potential function $f_Q(x_j, x_i)$ can be effectively viewed as the edge-weight between the vertex pair $x_j$-$x_i$. This will provide, later on in this disclosure, a means to perform a maximum-likelihood estimation (MLE) on the vertex-set $Y \in G_M$ based upon the vertices $X \in G_Q$. Moreover, processor 210 can constraint this process using the metrics on the manifolds M and Q. Recall that, in Equation 1 we expressed the vertex $x_j$ as a sum over the product $\mathbb{I}(x_j:y_j)\Gamma(y_k)$. If the actual correspondences $x_j:y_j$ are not in hand, we can employ the prior $\eta_j$ so as to relax Equation 1 and write $$x_j = \sum_{y_k \in Y} \eta_j \mathcal{K}(y_k, \xi_j) \quad (3)$$

where $\mathcal{K}(\bullet)$ is a kernel function with parameter set $\xi_j$. FIG. 6 provides an intuitive interpretation to this relaxation process. Note that $\xi_j$ is now, in practice, a kernel variable on the manifold M 602 which has a correspondence relationship to the vertex $x_j$ 606.

Figure 6B:
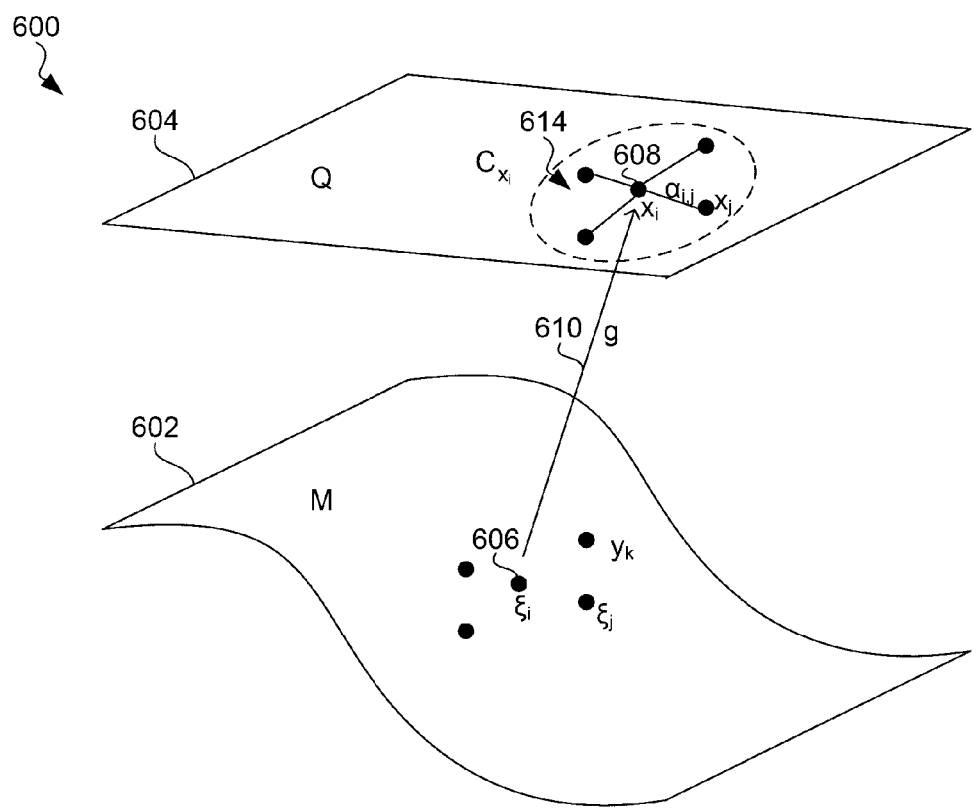

FIG. 6b illustrates the result of this treatment, where the vertices in $G_Q$ 614 correspond to each of the parameter vectors $\xi_j$, which, in turn, are supported by the vertex set Y. By substituting Equation 3 into Equation 2, we get $$P(x_i \mid C_{x_i}, Y) = \frac{1}{Z_Q} \prod_{x_j \in C_{x_i}} f_Q \left( \sum_{y_k \in Y} \eta_j \mathcal{K}(y_k, \xi_j), x_i \right) \quad (4)$$

The equation above is telling since it implies that, by using the cliques in $G_Q$, the vertex sets X and Y, a maximum likelihood estimate of the parameter $\xi_j$ can be obtained based upon our choice of kernel and potential functions.

Parameter Learning

Moreover, note that the potential function $f_Q(\bullet)$ are defined in the probability space corresponding to X, i.e. the graph $G_Q$ 614, whereas the kernel function $\mathcal{K}(\bullet)$ and the parameter vector $\xi_j$ are supported by the graph $G_M$ 612. This opens-up the possibility to recover the parameter vector-set making use of maximum likelihood estimation. Once these are in hand, the vertices of the graph $G_M$ can be mapped onto the manifold Q based upon the topology of the graph $G_M$.

To take our analysis further, we note that, since the vertex-set for the graph $G_Q$ 614 is a Gibbs Field, it should follow a Gibbs distribution. Hence, processor 210 employs the potential function $$f_Q(x_j, x_i) = \sum_{y_k \in Y} \alpha_{i,j} \exp\left\{ -\frac{1}{T} d_M(y_k, \xi_j)^2 \right\} \quad (5)$$

where $d_M(\bullet)^2$ is the squared geodesic distance on the Manifold M. That is, $d_M(\bullet)^2$ is a measure of similarity between pixel locations with respect to the input pixel values as indicated by the index M. In other examples, the measure of similarity may be a difference in pixel labels or ordering of the pixels. Using the measure of similarity between pixel locations with respect to the input pixel values in the above and the following calculations two pixel locations that are similar with respect to the input values $y_i$ are also similar with respect to the determined values $x_i$. $\alpha_{j,k}$ are pairwise mixture weights, and the temperature T controls the sharpness of the distribution. With the equation above, we can write the likelihood as follows $$P(x_i \mid C_{x_i}, Y) = \frac{1}{Z_Q} \prod_{x_j \in C_{x_i}} \sum_{y_k \in Y} \alpha_{i,j} \exp\left\{ -\frac{1}{T} d_M(y_k, \xi_j)^2 \right\} \quad (6)$$

We can view the MLE task at hand as that corresponding to a mixture model which can be tackled using the EM algorithm. The idea underpinning the EM algorithm is to recover maximum likelihood solutions to problems involving missing or hidden data. To do this, processor 210 uses the parameter vectors $\xi_j$ as a set of variables to be estimated and the mixture weights $\alpha_{i,j}$ as the posterior probabilities that the vertex $x_j$ belongs to the $j^{th}$ component of the mixture.

Since the EM algorithm is an iterative one, processor 210 commences by indexing the expected log-likelihood to iteration number t. In the M-step, processor 210 aims at maximising the expected log-likelihood with respect to the parameter variables. This yields $$\xi_j^{t+1} = \frac{\sum_{\substack{y_k \in Y \\ x_k \in C_j}} \alpha_{k,j}^t \exp\left\{-\frac{1}{T} d_M(y_k, \xi_j^t)^2\right\} y_k}{\sum_{\substack{y_k \in Y \\ x_k \in C_j}} \alpha_{k,j}^t \exp\left\{-\frac{1}{T} d_M(y_k, \xi_j^t)^2\right\}} \quad (7)$$

In the E-step, processor 210 estimates the posterior probabilities. For the likelihood in Equation 6, this yields $$\alpha_{i,j}^{t+1} = \frac{\tau_i \sum_{\substack{y_k \in Y \\ x_k \in C_i}} \alpha_{k,j}^t \exp\left\{-\frac{1}{T} d_M(y_k, \xi_j^t)^2\right\}}{\sum_{x_l \in X} \tau_l \sum_{\substack{y_k \in Y \\ x_k \in C_i}} \alpha_{k,j}^t \exp\left\{-\frac{1}{T} d_M(y_k, \xi_j^t)^2\right\}} \quad (8)$$

where $\tau_i$ can be viewed as the posterior for each of the cliques in the graph. This is given by $$\tau_i = \frac{\sum_{x_k \in C_i} \alpha_{k,i}^t}{\sum_{\substack{x_l \in X \\ x_k \in C_i}} \alpha_{l,k}^t} \quad (9)$$

Note that, so far, Equations 7-9 make use of an unsupervised learning approach such that the topology of the graph $G_Q$ 614 constrains the inference process through its clique-set, whereas the parameter vectors $\xi_i$ govern the kernel function $\mathcal{K}(\bullet)$.

Energy Functions

It is worth noting in passing that the use of the potential function in Equation 5 corresponds to a Gibbs measure. This accounts for a Boltzmann distribution whose energy is the squared geodesic distance $d_M(\bullet)^2$. This can be seen by writing $$f_Q(x_j, x_i) = \alpha_{i,j} \sum_{y_k \in Y} \exp\left\{-\frac{1}{T} E_{\xi_j}(y_k)\right\} \quad (10)$$

where $E_{\xi_j}(y_k) = d_M(y_k, \xi_j)^2$ is the energy of $y_k$ with respect to the parameter vector $\xi_j$ and $\alpha_{i,j}$ is a function of the vertex-pair $x_i$-$x_j$. Note that, for instance, in Equation 5, it is possible to set $\alpha_{i,j} = \eta_i \eta_j$ to so as to write $f_Q(x_j, x_i) = \eta_i \eta_j \mathcal{K}(y_k, \xi_j)$ such that $$\mathcal{K}(y_k, \xi_j) = \sum_{y_k \in Y} \exp\left\{-\frac{1}{T} d_M(y_k, \xi_j)^2\right\} \quad (11)$$

This treatment opens up the possibility of using other kernels such as box functions or robust estimators.

Relation to Self-Organizing Maps

Note that other energy functions may be used. Moreover, the alpha weights may not need to be estimated but rather can be computed from the vertex-set X. In such cases, the inference process presented earlier is reminiscent of a self-organizing map (SOM).

Consider a Sampling Process in M and Set $$\alpha_{i,j} = \mathbb{1}[(x_j \sim \rho) h\left(\frac{1}{T} d_Q(x_i, x_j)^2\right)] \quad (12)$$

where $h(\bullet)$ is a real-valued positive function, $d_Q(x_i, x_j)$ is the geodesic distance on Q between the vertices $x_i$ and $x_j$, T is, as before, the temperature of the system and $\mathcal{K}(x_j \sim \rho)$ is an indicator function which is unity for the vertex $x_j$ corresponding to the parameter variable $\xi_j$ whose distance to the sample $y_k$ is minimum, i.e. the best matching unit $\rho$, and zero otherwise.

Moreover, consider the case where the energy function $E_{\xi_j}(y_k)$ is constant. Processor 210 performs the sampling process such that the update strategy in Equation 8 will draw the parameter vector $\xi_j^{t+1}$ towards the vector $\xi_\rho^t$ corresponding to the vertex $\rho$ in $G_Q$ 604 which is closest to the input sample $y_k$, i.e. the neighbours of the best matching unit $\rho$.

The resulting scheme is also consistent to the notion that, as the system "cools down", the influence of the geodesic distance upon the update decreases.

FIGS. 7a to 7h illustrate the 2-dimensional responses, visualised using the dot size as an output value. In other examples, the red-green colour space may be used. When only the best matching unit is used for the inference process and the distance on Q in Equation 12 is given by $d_Q(x_j, x_j)^2 = (x_j - x_j)^2$ (SOM-Euclidean) or $d_Q(x_i, x_j)^2 \equiv a$, where a is a constant (SOM-Constant). This, from the structural point of view, can also be viewed as the case where the edge-weights over each of the cliques in the graph $G_Q$ 614 are given by an exponential function or a constant, respectively. In the figure, uniformly distributed vertices are used, i.e. units, and, for the clique size $|C_{x_i}|$, processor 210 linearly decreased the number of nearest neighbours on each dimension of the red-green lattice which is then represented by dot size. This is provided for the sake of simplicity and so as to provide a direct analogy to a 2-dimensional SOM.

FIGS. 7d, 7f and 7h, also show the input in pseudo-colour as computed using the colour matching functions of Stiles and Burch, the visualisation delivered by the three principal components (PCA, FIG. 7b) of the spectra when these are used as pixel colour values and the mapping delivered by the proposed method (FIG. 7h) when $$\alpha_{i,j} = \frac{1}{T} \exp\left\{-\frac{1}{T}(x_i - x_j)^2\right\}, \text{ i.e. } d_Q(x_i, x_j)^2 = (x_i - x_j)^2$$

in Equation 12.

Visualisation

For all the methods in FIGS. 7a to 7h processor 210 may use a linear cooling schedule, i.e. the temperature T decreases at regular intervals throughout the update process. The figures also show the states of the graph on Q as it converges over 50000 iterations (FIGS. 7c, 7e, 7g). In each of the panels, the top-left map corresponds to iteration t=12500, top-right to t=25000, bottom-left to t=37500 and bottom-right to the final, i.e. 50 000th, update. In these figures, the graph nodes are distributed in a lattice and, for visualisation purposes, processor 210 may encode the colour using the parameter vector $\xi_j$ as follows $$u = \sum_{y_k \in Y x_k \in C_\rho} \exp\left\{-\frac{1}{T} d_Q(x_k, \rho)^2\right\} \exp\left\{-\frac{1}{T}(y_k - \xi_\rho)^2\right\} \quad (13)$$

where the use of $\xi_\rho$ and $C_\rho$ implies that the parameter variable and clique under consideration corresponds to the best matching unit $\rho$. Note that u is essentially the potential function $f_Q(\cdot)$ presented earlier when Equations 11 and 12 are combined and the corresponding distance and indicator functions are applied accordingly.

Note that, for the methods in FIGS. 7c to 7h, i.e. SOM-Euclidean, SOM-Constant and the proposed method, the final parameter vectors $\xi_j$ are organised in a similar manner. This is due to the similarities between the distance functions used in the three methods under consideration. Processor 210 may use a SOM-like training process to recover the variables $\xi_j$ and the use of the clique information for the evaluation of the potential functions for testing once the parameter vectors are in hand. This, in effect, delivers a means for a computationally efficient training stage while delivering the advantages of using clique information for the testing of the spectra.

This is more evident by visualising a natural scene from the imagery using the $\xi_j$ vectors as pixel values.

FIG. 8a illustrates the pseudocolour and detail (also in pseudocolour) of a natural scene from the imagery described. FIG. 8b illustrates the visualisation of the input image and its detail using the $\xi_j$ variables as pixel values for the case when only the best matching unit is used. FIG. 8c illustrates the visualisation of the input image and its detail using the $\xi_j$ variables as pixel values for the case when clique information are used.

In FIGS. 8a, 8b and 8c, processor 210 has recovered the coding vectors $\xi_j$ using the SOM-Constant alternative presented above. The top row of each figure, from left-to-right, shows the input image and the visualisation induced by the use of the clique contributions by method 300 as compared with that of the best matching unit alone. The bottom row shows the detail corresponding to the square 802 on the input image, for the visualisation in the top row. From the figures, it becomes evident that the use of the contribution of the vertices in the clique $C_\rho$ in Equation 13 in method 300 better preserves detail while still delivering a sharp differentiation between materials in the scene.

In one example, multispectral sensor 202 is equipped with a tuneable liquid-crystal filter and contains 33 bands in the range of 400 nm to 720 nm with an effective spatial resolution of approximately 1020×1340 pixels.

In another example, the input image comprises 31 bands in the visible range at 10 nm intervals or 191 bands in the spectral range of 400 nm-2475 nm. In one example, processor 210 performs a preprocessing step, by normalising the spectral vectors (image pixels) to unit $L_2$ norm.

In one example implementation, for the sake of efficiency, processor 210 trains using a SOM-like scheme. The graph $G_Q$ may be a three-dimensional lattice with an initial clique size of $10^3$, i.e. 10 neighbours per dimension. Processor 210 randomly samples 100,000 image spectra and uses a linear cooling schedule. Likewise, the clique size decreases linearly in each dimension as the iteration number increases. This is in accordance to SOM training, with a linear decay in both learning rate and neighborhood radius.

Based on the learned parameter vectors, processor 210 can then infer material prototypes as well as a global segmentation of the image according to material associations. To do this, processor 210 first performs clustering on the vectors $\xi_j$ using a mode-seeking algorithm. Each image spectrum can then be associated to a cluster given the mapping described in Eq. 1.

Furthermore, the modes obtained during clustering can be seen as the material prototypes of the scene. Here, processor 210 employs an efficient variant of mean shift, i.e. Fast Adaptive Mean Shift (FAMS). This choice is based on the fact that FAMS is well suited for a high dimensional feature space by using adaptive bandwidths and a fast nearest-neighbor approximation during its kernel density estimation. As the feature space only contains of $10^3=1000$ vectors, processor 210 can abstain from the nearest neighbour approximation.

The bandwidth for each data point $\xi_j$ may be chosen so that $k=0.6\sqrt{|X|}$ nearest neighbours lie within its bounds. Additionally, processor 210 weights the bandwidth of each $\xi_j$ by the number of image spectra $y_k$ that are associated with it. The rationale behind this is that, in this manner, an accurate approximation of the original spectral distribution can be easily obtained.

In another example, processor 210 perform a 1:2 subsampling of the images (a 4-fold reduction of image size without smoothing).

FIG. 9a illustrates three example inputs and 9b illustrates material segmentation results based upon the abundance of each material scene at each pixel location, i.e. the material associations for each pixel. In the figure, the segment colours have been randomly assigned. Method 300 is capable of discerning most relevant materials in the scene.

FIGS. 10a and 10b depict the material prototypes found in the images as shown in FIG. 9a. These prototypes are derived from the clustering results as follows. Processor 210 uses a mode-seeking algorithm so as to take advantage of the parameter vectors directly.

FIG. 10a illustrates the image spectra of the images in FIG. 9a. This shows the visualization of the normalised image spectra using the Parallel Coordinates method of the Gerbil hyperspectral visualization framework. In the plot, all the spectra contained in the image are used to obtain a spectral power histogram. FIG. 10b shows the extracted prototypes using method 300.

We can observe that both methods succeed in capturing the prominent materials in the scene as the extracted prototypes give a good hint at the respective image's spectral power distribution. It is noted that the proposed mode-seeking approach is devoid of user input parameters, which is an advantage over other methods.

Distance Preservation

We now turn our attention to a qualitative analysis of the mapping $\Gamma: \Re^m \mapsto \Re^q$. Recall that, as described in Eq. 1, method 300 provides a mapping from a manifold with dimension m to one of dimensionality q. m accounts for the number of wavelength indexed bands in the imagery and q=3, for example. By assuming local linearity in the mapping between the manifolds M and Q (this is reasonable due to the use of the equivalent of Euclidean distance functions $d_M(\bullet)$ and $d_Q(\bullet)$), processor 210 can assess the relationship between distances on both manifolds employing the notion that those spectral radiance vectors $y_j$ that are close in M should be linked to vectors $x_j$ on the proposed mapping that are, likewise, close to one another in Q.

To evaluate this property, for each pixel $y_j$ in an image, processor 210 randomly selects 40 other pixels and, for each of those selected $y_i$, processor 210 computes $\|y_i - y_2\|$ as well as $\|u-v\|_2$, where u and v correspond to the visualisation vectors for $y_i$ and $y_j$, respectively, computed using Eq. 13.

In this manner, the resulting distance pairs can be computed so as to assess the linearity of the distance relationships induced by the mapping Γ.

FIGS. 11a, 11b and 11c illustrate scatter plot histograms for the pairwise distances induced by the mapping Γ. In the plots, the bar indicates the frequency-grey scale. The figure shows plots for three images taken from each of the datasets under consideration. This is provided to explore the effects of spectral and spatial resolution on the linearity of Γ.

The figures show that small distances exhibit a high correlation for the three images. Larger distances diverge slightly from a strictly linear relationship. This is somewhat expected since underlying manifolds may not be well approximated by a Euclidean metric as the pairwise distances increase.

Running Times

One approach to obtain a similar clustering would be to run the mean shift algorithm directly on the normalized image spectra. The mean shift has a computational complexity of $O(n^2)$ in the number of pixels. In some examples, over 95% of the computation time for the mean shift is spent on the vector distance calculation. This makes the high dimensionality of multispectral data an additional burden to the method.

This contrasts with method 300, where processor 210 effectively finds a sparse representation of the spectral distribution first and then run mean shift on a reduced data set.

Computer system 204 may be an Intel Core i7-2600 CPU and 16 GB RAM.

Processor 210 performs an unsupervised method for learning the materials in a scene from imaging spectroscopy data. Processor 210 performs a structural unsupervised statistical learning method where the inference process is effected using the EM algorithm. Method 300 may be used to recover material prototypes, perform scene material segmentation, visualization and dimensionality reduction. Input image data may comprise imagery acquired in lab environments, real-world settings and remote sensing platforms. Moreover, method 300 provides a margin of improvement as compared to a state-of-the-art method for material association recovery, being more computationally efficient in terms of computational power and memory use.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

The invention claimed is:

1. A computer implemented method for processing hyperspectral or multispectral image data, the image data comprising for each pixel location a sampled image spectrum that comprises multiple first values for each pixel location such that each of the multiple first values is representative of an intensity associated with a wavelength index, the method comprising:

determining for each pixel location a coding vector from the multiple first values to one or more second values based on a measure of similarity between pixel locations with respect to the multiple first values, the measure of similarity based on the coding vector, such that two pixel locations that are similar with respect to the multiple first values are also similar with respect to the one or more second values;

storing for each pixel location the determined one or more second values associated with that pixel location on a data store; and outputting a visual image of the image data by using the one or more second values as intensity values for one or more respective output channels.

2. The method of claim 1, wherein the measure of similarity between pixel locations with respect to the multiple first values is based on a distance measure between a vector formed by the multiple first values and the coding vector.

3. The method of claim 1, wherein determining the coding vector comprises performing a maximum likelihood estimation.

4. The method of claim 3, wherein performing the maximum likelihood estimation comprises performing an Expectation Maximisation method.

5. The method of claim 4, wherein performing the Expectation Maximisation method comprises performing an Expectation step by determining an updated mapping vector and an updated mixture weight in relation to the one or more second values and performing a Maximisation step by determining a posterior of each clique of pixel locations.

6. The method of claim 1, further comprising determining mixture weights in relation to the one or more second values by applying a self organising map.

7. The method of claim 1, wherein the number of the one or more second values is less than the number of the multiple first values.

8. The method of claim 1, further comprising determining multiple clusters of the pixel locations based on the one or more second values.

9. The method of claim 8, further comprising associating a material spectrum with each cluster.

10. The method of claim 1, wherein the one or more second values comprise red, green and blue values.

11. The method of claim 1, wherein the number of the multiple first values is more than 7.

12. A non-transitory computer-readable medium, including computer-executable instructions stored thereon that when executed by a processor causes the processor to perform the method of claim 1.

13. A computer system for processing hyperspectral or multispectral image data, the computer system comprising:
   a data port to receive the image data comprising for each pixel location a sampled image spectrum that comprises multiple first values for each pixel location such that each of the multiple first values is representative of an intensity associated with a wavelength index;
   a processor determining for each pixel location a coding vector from the multiple first values to one or more second values based on a measure of similarity between pixel locations with respect to the multiple first values, the measure of similarity based on the coding vector, such that two pixel locations that are similar with respect to the multiple first values are also similar with respect to the one or more second values and outputting a visual image of the image data by using the one or more second values as intensity values for one or more respective channels; and
   a data store, for storing each pixel location of the visual image.

* * * * *

UNITED STATES PATENT AND TRADEMARK OFFICE
CERTIFICATE OF CORRECTION

PATENT NO. : 10,007,856 B2
APPLICATION NO. : 15/118643
DATED : June 26, 2018
INVENTOR(S) : Antonio Robles-Kelly et al.

It is certified that error appears in the above-identified patent and that said Letters Patent is hereby corrected as shown below:

In the Specification

Column 1, Lines 52-54, the following text should be deleted:
"by a second sample 132 in the spectral space 130. In this way, the radiance spectra of many pixels can be represented in the same spectral space 130."

Column 7, Lines 43-45, Should Read As Follows:
"where $Y$ is the vertex set of $G_M$, $\Gamma(\cdot)$ is a mapping function such that $\Gamma:\Re^m$ a $\Re^q$ and $I(x_j : y_j)$ is an indicator function which is unity if $x_j$ is adjacent to $y_j$ and zero otherwise."

Column 7, Line 50, Should Read As Follows:
"graph. Consider the clique $C_{x_i}$ centered at the vertex $x_i$."

Column 8, Line 2, Should Read As Follows:
"expressed the vertex $x_j$ as a sum over the product $I(x_j : y_j)\Gamma(y_k)$."

Column 9, Line 8, Should Read As Follows:
"that the vertex $x_i$ belongs to the $j^{th}$ component of the mixture."

Column 10, Line 23, Should Read As Follows:
"is, as before, the temperature of the system and $I(x_j : \rho)$ is"

Column 10, Line 42, Should Read As Follows:
"and the distance on $Q$ in Equation 12 is given by $d_Q(x_i, x_j)^2 = (x_i - x_j)^2$ (SOM-Euclidean) or $d_Q(x_i, x_j)^2 \equiv a$, where $a$ is a"

Signed and Sealed this
Twentieth Day of November, 2018

Andrei Iancu
*Director of the United States Patent and Trademark Office*